United States Patent
Götz et al.

(10) Patent No.: US 6,727,385 B1
(45) Date of Patent: Apr. 27, 2004

(54) METHOD FOR PRODUCING O-CHLOROMETHYL BENZOIC ACID CHLORIDES

(75) Inventors: Roland Götz, Neulussheim (DE); Norbert Götz, Worms (DE); Michael Keil, Freinsheim (DE); Bernd Wolf, Fussgonheim (DE); Adrian Steinmetz, Mannheim (DE); Armin Stamm, Nieder-Olm (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/130,825
(22) PCT Filed: Nov. 27, 2000
(86) PCT No.: PCT/EP00/11810
§ 371 (c)(1), (2), (4) Date: Aug. 12, 2002
(87) PCT Pub. No.: WO01/42182
PCT Pub. Date: Jun. 14, 2001

(30) Foreign Application Priority Data

Dec. 7, 1999 (DE) .......................... 199 58 758
Feb. 19, 2000 (DE) .......................... 100 07 695

(51) Int. Cl.$^7$ .............................................. C07C 55/36
(52) U.S. Cl. ...................................................... 562/853
(58) Field of Search ................................. 562/853, 856

(56) References Cited

FOREIGN PATENT DOCUMENTS

EP    676 389    10/1995
WO    99/16743    4/1999

*Primary Examiner*—Paul J. Killos
(74) *Attorney, Agent, or Firm*—Keil & Weinkauf

(57) ABSTRACT

A process for preparing o-chloromethylbenzoyl chlorides of the formula I,

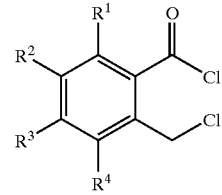

in which $R^1$ to $R^4$ can be identical or different and are hydrogen, $C_1$–$C_4$-alkyl, halogen or trifluoromethyl, by reacting benzo-fused lactones of the formula II,

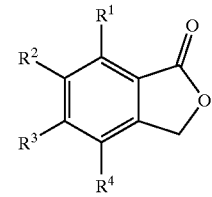

in which $R^1$ to $R^4$ are as defined above, with thionyl chloride, which comprises carrying out the reaction in the presence of catalytic amounts of boric acid, boric anhydride, borate, boronic acid or boronic acid esters and catalytic amounts of a quaternary ammonium salt is described.

5 Claims, No Drawings

METHOD FOR PRODUCING O-CHLOROMETHYL BENZOIC ACID CHLORIDES

The present invention relates to a process for preparing o-chloromethylbenzoyl chlorides of the formula I,

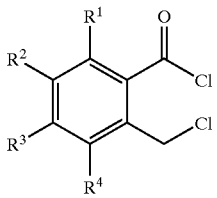

in which $R^1$ to $R^4$ can be identical or different and are hydrogen, $C_1$–$C_4$-alkyl, halogen or trifluoromethyl, by reacting benzo-fused lactones of the formula II,

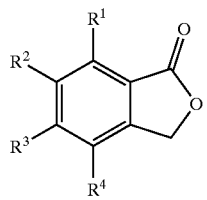

in which $R^1$ to $R^4$ are as defined above, with thionyl chloride.

o-Chloromethyl-substituted benzoyl chlorides are important intermediates for preparing, for example, pesticidally active compounds, as described in the patents EP-A 460 575, EP-A 463 488, WO-A 95/18789, WO-A 95/21154 and WO-A 97/15552.

o-Chloromethyl-substituted benzoyl chlorides can be prepared, for example, by reacting benzo-fused lactones with thionyl chloride or phosgene. If thionyl chloride is used, the apparatus to be employed is simplified and safety precautions can be reduced.

EP-A 676 389 describes the preparation of o-chloromethylbenzoyl chlorides from benzo-fused lactones using thionyl chloride in the presence of a nitrogen compound. To achieve a satisfactory conversion, reaction temperatures of 160–170° C. are required, at which thionyl chloride is already partially decomposed, resulting in the formation of troublesome byproducts. Furthermore, addition of gaseous hydrochloric acid is required. Finally, in some cases the yields are considerably less than 90%.

In WO-A 99/16743, the reaction with thionyl chloride is carried out in the presence of $BF_3$ etherate and a quaternary ammonium salt at 90–100° C. It is found to be disadvantageous here that $BF_3$ etherate is highly sensitive to moisture and may also liberate diethyl ether in the course of the reaction. Diethyl ether has a low boiling point, is readily combustible and tends to form peroxides. Moreover, by hydrolysis of boron trifluoride, it is possible for hydrogen fluoride (hydrofluoric acid), which is highly corrosive and causes problems, in particular with respect to the materials used, to be formed. Implementation on an industrial scale would therefore require special apparatus.

It is an object of the present invention to provide an economical process, suitable for industrial implementation, for preparing o-chloromethylbenzoyl chlorides which does not have the abovementioned disadvantages and still affords high yields.

We have found that this object is achieved by the process mentioned at the outset, which comprises carrying out the reaction in the presence of catalytic amounts of a boron-containing catalyst selected from the group consisting of: boric acid, boric anhydride, borate, boronic acid, boronic acid esters and catalytic amounts of an ammonium salt.

The starting materials used are benzo-fused lactones (phthalides) of the formula II,

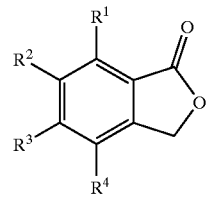

in which $R^1$ to $R^4$ can be identical or different and are hydrogen (H), $C_1$–$C_4$-alkyl, halogen (fluorine, chlorine, bromine or iodine) or trifluoromethyl. Preference is given to using unsubstituted phthalide.

Suitable quaternary ammonium salts are, in particular, quaternary ammonium halides, such as, for example, tetraalkylammonium chlorides or bezyltrialkylammonium chlorides. Particularly suitable are: tetramethylammonium chloride, tetraethylammonium chloride, tetrabutylammonium chloride, benzyltrimethylammonium chloride, benzyltriethylammonium chloride, benzyltributylammonium chloride, N,N-dimethylpiperidininum chloride. Particular preference is given to benzyltriethylammonium chloride.

The quaternary ammonium salts are generally added in amounts of from 0.1 to 20 mol %, based on the amount of benzo-fused lactone used, preferably in amounts of from 0.5 to 10 mol %.

The reaction is furthermore carried out in the presence of catalytic amounts of boric acid, boric anhydride, borate, boronic acid or boronic acid esters. Suitable boronic acids/esters are the following compounds: arylboronic acid (in particular phenylboronic acid), arylboronic acid $C_1$–$C_4$-alkyl esters, $C_1$–$C_6$-alkylboronic acid or $C_1$–$C_4$-alkylboronic acid $C_1$–$C_4$-alkyl esters. suitable borates are in particular alkali metal berates, such as borax.

Particular preference is given to using boric acid. Such processes give excellent yields and have the advantage that the reaction mixtures are free of fluoride ions. Thus, it is not possible for hydrofluoric acid (hydrogen fluoride) to be formed in the course of the reaction. Compared to the analogous reaction where the Lewis acid used is a $BF_3$ derivative, the entire apparatus is simplified.

The boric acid is added in amounts of from 0.1 to 20 mol %, based on the amount of benzo-fused lactone (phthalide) employed, preferably in amounts of from 0.5 to 10 mol %.

Based or the phthalide II in general from 1 to 1.5 equivalents of thionyl chloride are used.

The thionyl chloride can be charged initially together with the other reactants (batch process), or be metered in in the course of the reaction over preferably 1–8 hours (semi-batch process). Furthermore, it is possible to carry out the reaction continuously.

If desired, it is possible to introduce gaseous hydrogen chloride to accelerate ring-opening. However, introduction of hydrogen chloride during the synthesis is preferably dispensed with.

The reaction temperatures used are usually from 100 to 180° C. and preferably from 110 to 150° C.

The process is preferably carried out in the absence of a solvent. However, it is possible to add a solvent which is inert to thionyl chloride. Inert solvents are, for example, aromatic hydrocarbons, such as toluene, o-, m- or p-xylene or mixtures thereof, chlorinated aromatic hydrocarbons, such as chlorobenzene or dichlorobenzenes, or cyclic carbonates, such as ethylene carbonate or propylene carbonate. It is furthermore possible to use thionyl chloride itself as solvent which can be removed distillatively at the end of the reaction and be recycled into the process.

The reaction is generally carried out at atmospheric pressure or at a pressure of 1–10 bar.

The examples below serve to illustrate the process in more detail.

PROCESS EXAMPLES

General Procedure for Preparing o-chloromethylbenzoyl chloride

In a stirred apparatus consisting of a 1.6 l double-jacketed reactor fitted with a battery of high-efficiency condensers, in each case X mol of phthalide were initially charged with the catalyst system in question. 1.3 equivalents of thionyl chloride, based on the phthalide, were either charged together with the other components or added dropwise over a period of from 1 to 8 hours. The mixture was then stirred at reaction temperature for 1–15 hours. The content of the product of value in the crude mixture was determined by GC. In selected examples, the product was isolated by fractional distillation at 0.5 mbar and 75–85° C.

Example 1

268 g (2 mol) of phthalide, 12.4 g (0.2 mol, 10 mol %) of boric acid and 45.4 g (0.2 mol, 10 mol %) of benzyltriethylammonium chloride were initially charged in a stirred vessel and heated to 130° C. Over a period of 5 hours, 310 g (2.6 mol) of thionyl chloride were added dropwise to this melt. The reaction mixture was then stirred at 130° C. for another 5 hours. The reaction discharge contained 97 GC area % of o-chloromethylbenzoyl chloride.

Example 2

670 g (5 mol) of phthalide, 9.3 g (0.15 mol, 3 mol %) of boric acid and 34.1 g (0.15 mol, 3 mol %) of benzyltriethylammonium chloride were initially charged in a stirred vessel and heated to 130° C. Over a period of 5 hours, 774 g (6.5 mol) of thionyl chloride were added dropwise to this melt. The reaction mixture was then stirred at 130° C. for another 5 hours. Distillation of the reaction discharge gave 940 g (99.4% yield) of o-chloromethylbenzoyl chloride of a purity of 98.1% (GC).

We claim:

1. A process for preparing o-chloromethylbenzoyl chlorides of the formula I

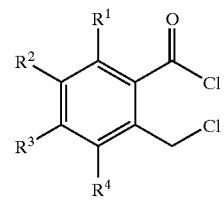

in which $R^1$ to $R^4$ can be identical or different and are hydrogen, $C_1$–$C_4$-alkyl, halogen or trifluoromethyl, by reacting benzo-fused lactones of the formula II

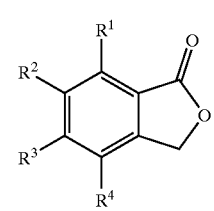

in which $R^1$ to $R^4$ are as defined above, with thionyl chloride, which comprises carrying out the reaction in the presence of
   i) catalytic amounts of a boron-containing catalyst selected from the group consisting of: boric acid, boric anhydride, alkali metal borate, boronic acid, boronic acid esters; and
   ii) catalytic amounts of a quaternary ammonium salt.

2. A process as claimed in claim 1, wherein the boron-containing catalyst is boric acid.

3. A process as claimed in claim 1, wherein the boron-containing catalyst is arylboronic acid, arylboronic acid $C_1$–$C_4$-alkyl ester, $C_1$–$C_6$-alkylboronic acid or $C_1$–$C_6$-alkylboronic acid $C_1$–$C_4$-alkyl ester.

4. A process as claimed in claim 1, wherein the boron-containing catalyst is employed in a concentration of from 0.1 to 20 mol %, based on the lactone II.

5. A process as claimed in claim 1, wherein from 0.1 to 20 mol % of the quaternary ammonium salt, based on the lactone II, are employed.

* * * * *